United States Patent
Barkley et al.

[11] Patent Number: 5,868,794
[45] Date of Patent: Feb. 9, 1999

[54] AED AND BATTERY PACK WITH ANTICIPATORY BATTERY DISENGAGEMENT DETECTION

[75] Inventors: Steven D. Barkley, Champlin; Robert K. Johnson, Blaine, both of Minn.

[73] Assignee: SurVivaLink Corporation, Minneapolis, Minn.

[21] Appl. No.: 57,312

[22] Filed: Apr. 8, 1998

Related U.S. Application Data

[60] Provisional application No. 60/041,807, Apr. 8, 1997.

[51] Int. Cl.[6] ....................................... A61N 1/39
[52] U.S. Cl. .................. 607/5; 607/36; 607/29; 607/63
[58] Field of Search .................. 607/2, 5, 6, 29, 607/27, 34, 36, 62, 63; 396/277; 702/63

[56] References Cited

U.S. PATENT DOCUMENTS

| | | |
|---|---|---|
| 4,590,943 | 5/1986 | Paull et al. ................................. 607/5 |
| 4,733,265 | 3/1988 | Haraguchi et al. .................... 354/484 |
| 5,224,870 | 7/1993 | Weaver et al. . |
| 5,350,317 | 9/1994 | Weaver et al. . |
| 5,470,343 | 11/1995 | Fincke et al. ............................... 607/5 |
| 5,483,165 | 1/1996 | Cameron et al. . |
| 5,741,305 | 4/1998 | Vincent et al. . |
| 5,762,512 | 6/1998 | Trant et al. ............................. 439/347 |

FOREIGN PATENT DOCUMENTS

WO 97/42669  11/1997  European Pat. Off. .

*Primary Examiner*—William E. Kamm
*Assistant Examiner*—Kennedy J. Schaetzle
*Attorney, Agent, or Firm*—Patterson & Keough, P.A.

[57] ABSTRACT

An AED includes a housing. Electronic circuitry is disposed in the housing for delivery of an electric shock to a stricken patient. A removable battery pack is selectively, operably, communicatively coupled to the electronic circuitry. The battery pack has an anticipatory detector for generating an anticipatory signal to the electronic circuitry. The signal indicates to the electronic circuitry that the disengagement of the battery pack from the AED is imminent. The present invention further includes a method for ensuring that the high voltage storage circuits of the AED are safely discharged prior to disengaging the battery pack from the AED.

20 Claims, 12 Drawing Sheets

AED AND BATTERY PACK WITH ANTICIPATORY BATTERY DISENGAGEMENT DETECTION

RELATED APPLICATIONS

This application claims the benefit of U.S. Provisional Application No. 60/041,807, filed Apr. 8, 1997 and incorporated herein in its entirety by reference.

TECHNICAL FIELD

The present invention relates to an automated external defibrillator (AED) and a battery pack that powers the AED. More particularly, the present invention is an AED and a battery pack, the battery pack being removable and containing a plurality of individual battery cells and is designed for use with the AED.

BACKGROUND OF THE INVENTION

There is a need in the industry for a battery pack for use with an AED. Preferably, the battery pack should have the following characteristics. The battery pack should be removably coupled to the AED. When coupled to the AED, the battery pack should be held semi-rigidly in place such that virtually no relative motion occurs between the battery pack and the AED. Additionally, the battery pack should be held securely in place once joined to the AED so that it is very unlikely that the battery pack will become inadvertently disengaged from the AED.

An AED typically uses integral batteries to power various electronic components of the AED and to generate the very high voltages necessary for shocking a patient. The AED has the capability of delivering very high voltage impulses to a stricken patient. Such voltages may exceed 2,000 volts. The high voltages are typically developed from the relatively low voltage battery by charging a capacitor bank prior to delivery of the shock to the patient. Removal of the battery pack from the AED removes power from the electronic components that provide control to the capacitor bank. If the battery is removed from the AED when the capacitors are charged to the high voltage, there is no control remaining over the ultimate discharge of the capacitors. Accordingly, in addition to the aforementioned characteristics, there is a need to sense the imminent removal of the battery from the AED and, while there is still power to the various electronic components and control remaining, to safely discharge the capacitors.

SUMMARY OF THE INVENTION

The AED of the present invention substantially meets the aforementioned needs. The AED is configured to sense the imminent removal of the battery from the AED and, while there is still power to the various electronic components and control remaining, safely discharge the capacitors of the AED. Means are provided to anticipate the disconnecting of the battery from the AED so that the discharge is accomplished in a controlled manner.

The AED of the present invention has a housing. Electronic circuitry is disposed in the housing for delivery of an electric shock to a stricken patient. A removable battery pack is selectively, operably, communicatively coupled to the electronic circuitry. The battery pack has an anticipatory detector for generating an anticipatory signal to the electronic circuitry. The signal indicates to the electronic circuitry that the disengagement of the battery pack from the AED is imminent. The present invention further includes a method for ensuring that the high voltage storage circuits of the AED are safely discharged prior to disengaging the battery pack from the AED.

DETAILED DESCRIPTION OF THE DRAWINGS

Referring to FIGS. 1–5, an emergency electronic device and, more particularly, an automated external defibrillator (AED) 10 with the ability to store rescue information may be appreciated. The stored rescue information may include patient data, AED operational data and/or sound recorded proximate AED 10.

As shown, AED 10 includes a plastic case 12 with a carrying handle 14 on the front portion. A battery compartment (as will be later described) in the rear portion of AED 10 encloses a battery pack 16, the battery pack 16 being removably disposed within the battery compartment. A visual maintenance indicator 20 and a data access door 22, which conceals a serial connector port 23 and a data card slot 24, (FIG. 3) are located on the outside of case 12 for easy access by an operator.

Figure 1:
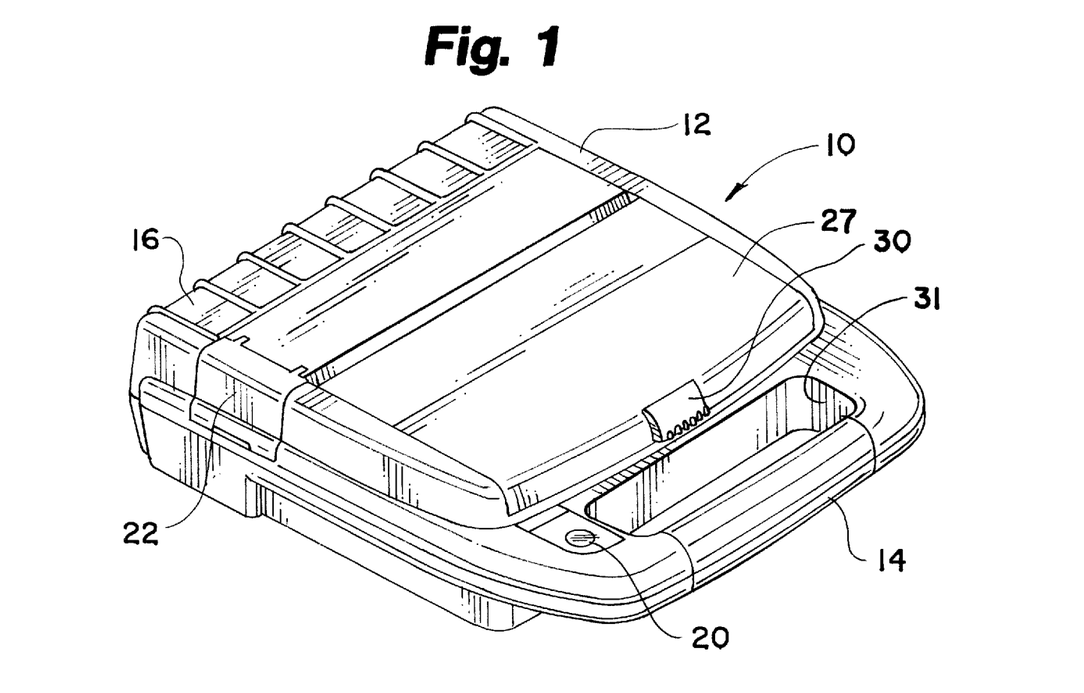
FIG. 1 is a perspective view of an automated external defibrillator.
Figures 2, 4:
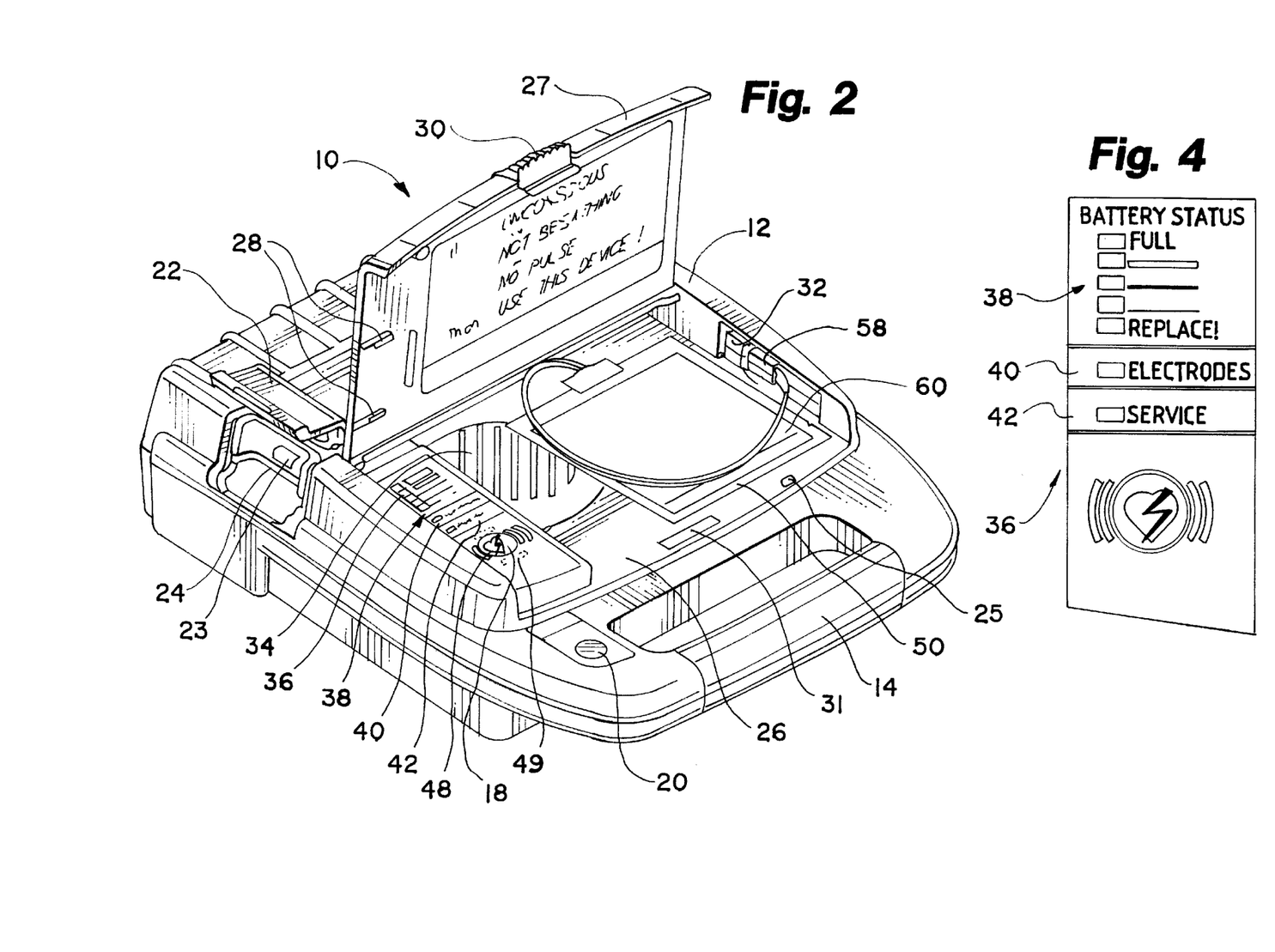
FIG. 2 is a perspective view of the AED of FIG. 1 having the lid opened.
FIG. 4 is a plan view of a diagnostic display of the AED.

Case 12 also includes an electrode compartment 26 defined in the top portion of case 12 (depicted in FIG. 2). An illuminatable rescue/resume switch 18 is disposed adjacent to electrode compartment 26. The electrode compartment 26 is closed by lid 27, lid 27 being mounted to case 12 by hinges (not visible). Lid 27 covers the rescue/resume switch 18 when the lid 27 is in the closed disposition, the closed disposition being depicted in FIGS. 1 and 3. The rescue/resume switch 18 is actually a single switch with illuminatable labels alternatively indicating the "resume" 49 or the "rescue" 48 function, "rescue" 48 appearing above the switch 18 and "resume" 49 appearing below the switch 18, depending on whether AED 10 is cuing the operator to perform a rescue or resume operation by activating switch 18.

A data card storage bracket 28 is formed on the inside of the lid 27 for holding a data card 29 for use in recording the parameters of a rescue intervention. The data card 29 is insertable into the data card slot 24, as indicated by Arrow A in FIG. 3. A bayonet-type releasable latch 30 holds lid 27 closed when AED 10 is not in use by engaging a receiving recess 31 (FIG. 2) defined in the floor of electrode compartment 26. Lid 27 is opened by grasping the underside of latch 30, pushing in to disengage latch 30 from recess 31 and lifting upward on latch 30 to gain access to electrode compartment 26. Opening the lid 27 activates a lid open switch 25. The lid open switch 25 may be any suitable switch such as a reed switch or a Hall effect switch.

An electrode connector 32, speaker 34 and diagnostic display panel 36 are disposed on case 12 within electrode compartment 26. The diagnostic display panel 36 is disposed adjacent to the illuminatable rescue/resume switch 18. Diagnostic display panel 36 includes visual "Battery Status" indicator light 38, "Electrodes" indicator light 40, and "Service" indicator light 42. An instruction and safety label is located in the inside surface of lid 27. Electrodes 50 are disposed within electrode compartment 26 and are removably connected to electrode connector 32 by connector 58. Electrodes 50 typically include a pair of electrodes for attachment to a patient in a sealed package 60.

Figure 5:
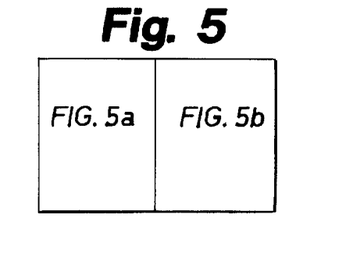
FIG. 5 is a block diagram of an electrical system of the AED.
Figure 5A:
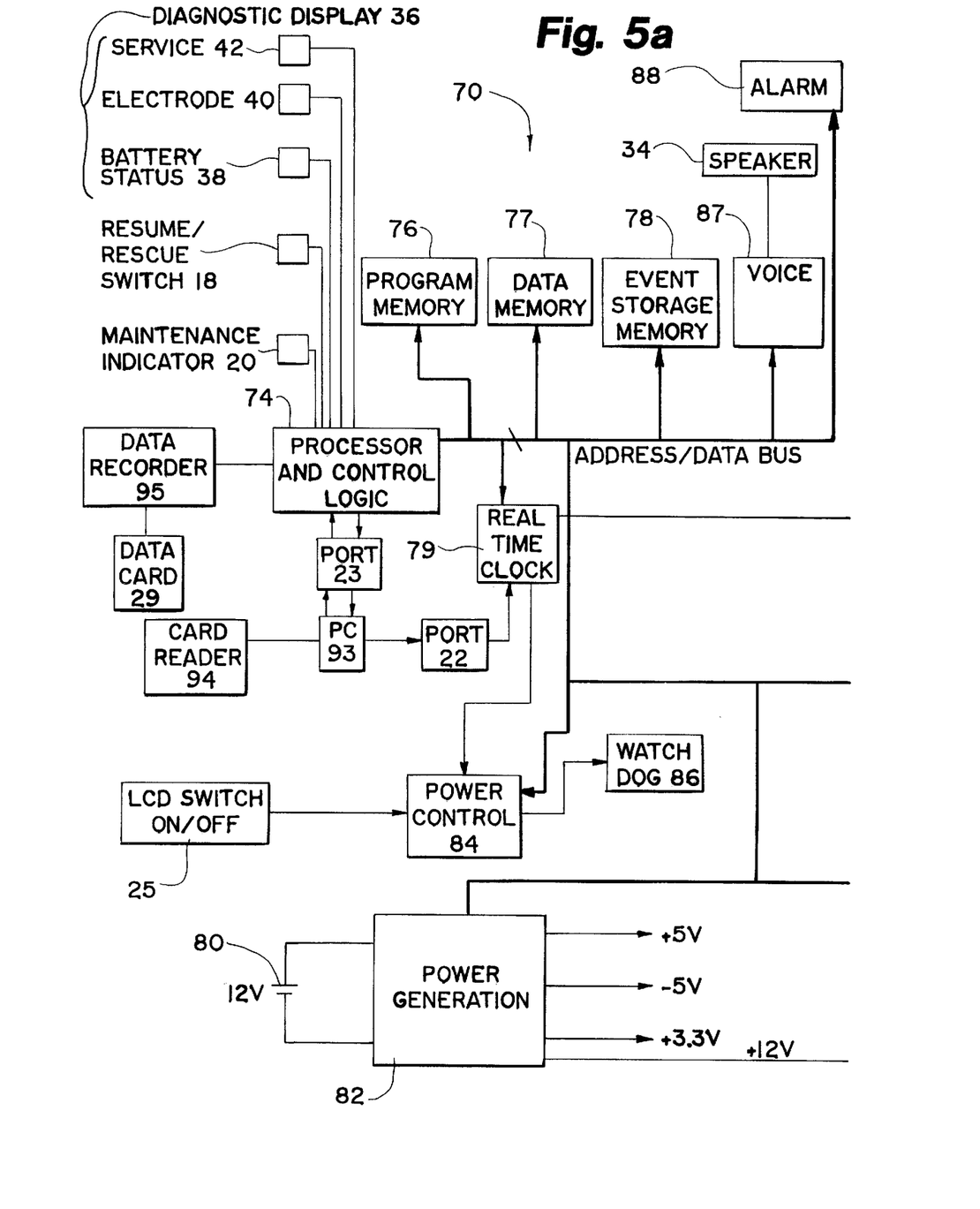
Figure 5B:
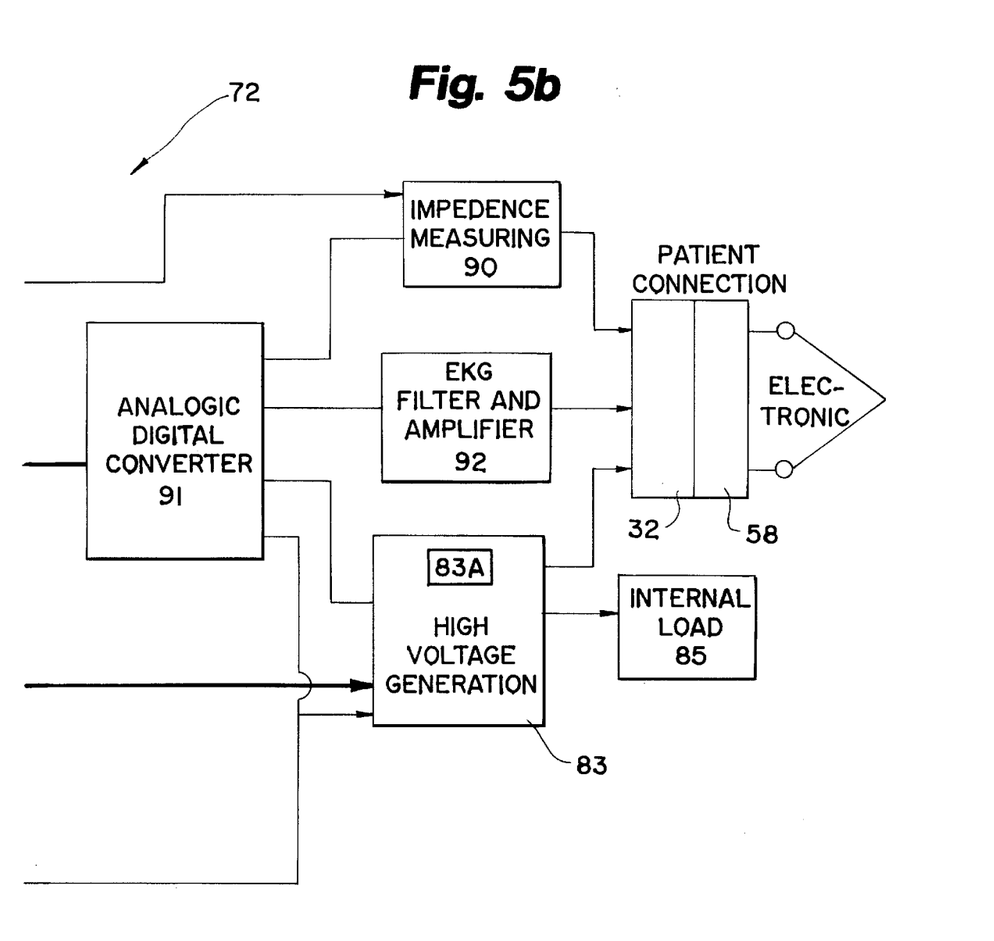

FIG. 5 is a block diagram of the electrical system 70 of AED 10. The overall operation of AED 10 is controlled by a digital microprocessor-based control system 72, which includes a processor 74 interfaced to program memory 76, data memory 77, event memory 78 and real time clock 79. The digital microprocessor-based control system 72 may be initiated by operation of the lid open switch 25 when the lid 27 is opened and may be deactivated by operation of the lid open switch 25 when the lid 27 is closed. The operating program executed by processor 74 is stored in program memory 76. Data memory 77 is used by processor 74 as a scratch pad memory during the execution of the operating program.

Electrical power is preferably provided by a lithium sulphur dioxide battery 80 which is enclosed in battery pack 16, battery pack 16 being removably positioned within the battery compartment. Battery 80 may be comprised of a plurality of battery cells that are electrically coupled together. Battery 80 is connected to power generation circuit 82. The "Battery Status" indicator light 38 indicates the charge status of battery 80 and prompts the operator to replace battery 80 when needed.

During normal operation, power generation circuit 82 generates a 12V supply and regulated ±5V and 3.3V supplies with the power provided by battery 80. The ±5V output of battery 80 functions as a back-up battery to power components of electrical system 70 during the execution of self-tests and to activate maintenance indicators and alarms (as described below). Although not separately shown in FIG. 5, power generation circuit 82 includes voltage level sensing circuits which are coupled to processor 74. The voltage level sensing circuits provide low battery level signals to processor 74, for illumination of the "Battery Status" indicator light 38.

Power generation circuit 82 is also connected to power control circuit 84 and processor 74. Power control circuit 84 is connected to lid switch 25, watch dog timer 86, real time clock 79 and processor 74. Lid switch 25 provides signals to processor 74 indicating whether lid 27 is open or closed. Serial connector port 23 is coupled to processor 74 for two-way serial data transfer using an RS-232 protocol. Rescue/resume switch 18 (and the "rescue" 48 and "resume" 49 indications thereof), maintenance indicator 20, and "Battery Status" indicator light 38, "Electrodes" indicator light 40, and "Service" indicator light 42 of diagnostic display panel 36, as well as Voice circuit 87 and piezoelectric audible alarm 88, are connected to processor 74. Voice circuit 87 is further connected to speaker 34. In response to voice prompt control signals from processor 74, voice circuit 87 and speaker 34 generate audible voice prompts to an operator.

High voltage generation circuit 83 is also connected to and controlled by processor 74. High voltage generation circuits, such as circuit 83, are generally known and disclosed, for example, in the commonly assigned Persson, et al. U.S. Pat. No. 5,405,361, which is hereby incorporated by reference. In response to charge control signals provided by the processor 74, high voltage generation circuit 83 is operated in a charge mode during which one set of semiconductor switches (not separately shown) causes a plurality of capacitors (also not shown), to be charged in parallel to about 400V each by the power supplied by power generation circuit 82. Once charged, and in response to discharge control signals provided by processor 74, high voltage generation circuit 83 is operated in a discharge mode during which the capacitors are discharged in series by another set of semiconductor switches (not separately shown) to produce the high voltage defibrillation pulses. The defibrillation pulses are applied to the patient through electrodes 50. The electrodes 50 are connected by connectors 58 to electrode connector 32, which is in turn connected to high voltage generation circuit 83. Under certain circumstances described below, processor 74 causes high voltage generation circuit 83 to be discharged through an internal resistive load 85 rather than connector 32 to electrodes 50.

Impedance measuring circuit 90 is connected to electrode connector 32 and real time clock 79, and is interfaced to processor 74 through analog-to-digital (A/D) converter 91. The impedance measuring circuit 90 receives a clock signal having a predetermined magnitude from clock 79, and applies the signal to electrodes 50 through connector 32. The magnitude of the clock signal received back from electrodes 50 through connector 32 is monitored by impedance measuring circuit 90. An impedance signal representative of the impedance present across electrode connector 32 is then generated by impedance measuring circuit 90 as a function of the ratio of the magnitudes of the applied and received clock signals (i.e., the attenuation of the applied signal). A relatively high resistance (e.g, greater than about two hundred ohms) will be present across connector 32 if the conductive adhesive on electrodes 50 is dried out, if electrodes 50 are not properly connected to connector 32, or if electrodes 50 are not properly positioned on the patient. The resistance across connector 32 will be between about twenty-five and on hundred and eighty ohms when fresh electrodes 50 are properly positioned on the patient with good electrical contacts. The impedance signal representative of the impedance measured by circuit 90 is digitized by A/D converter 91 and provided to processor 74.

Figure 3:
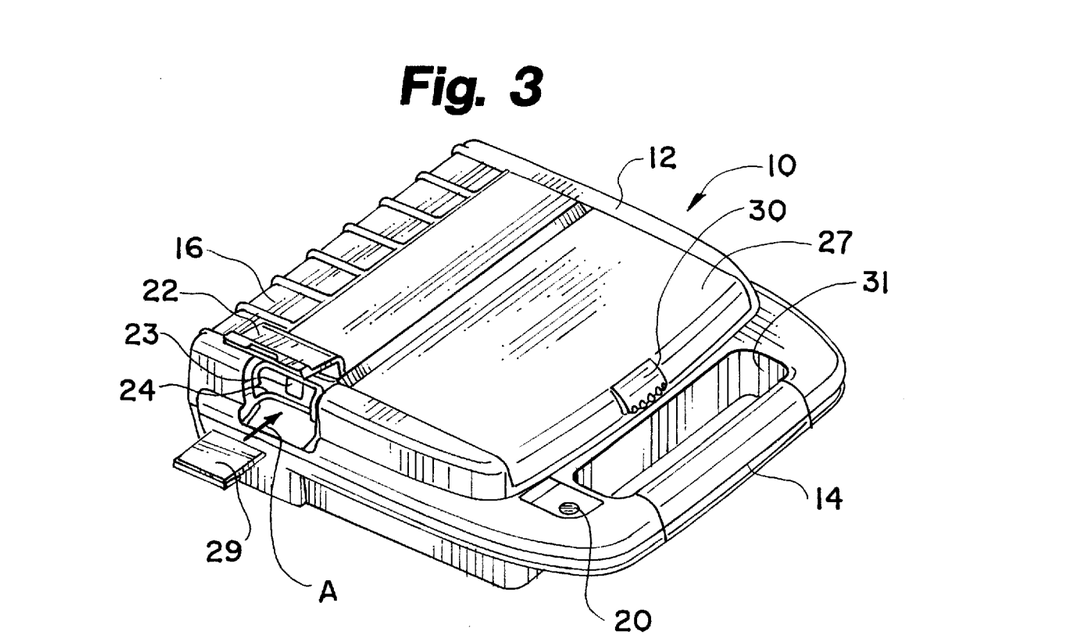
FIG. 3 is a perspective view of the AED having a rescue information data card positioned for insertion therein.

AED 10 also includes a data recorder 95 that is interfaced to processor 74 and positioned internally within AED 10 adjacent to data card slot 24 so as to be ready to accept data card 29, as depicted in FIG. 3. AED 10 further includes an electrocardiogram (EKG) filter and amplifier 92 which is connected between electrode connector 32 and A/D converter 91. The EKG or cardiac rhythm of the patient, sensed at the electrodes 50, is processed by filter and amplifier 92 in a conventional manner, and digitized by A/D converter 91 before being coupled to processor 74.

The rescue mode operation of AED 10 is initiated when an operator opens lid 27 to access electrodes 50. The opening of lid 27 is detected by lid switch 25. In response to this action, power control circuit 84 activates power generation circuit 82 and initiates the rescue mode operation of processor 74. Processor 74 then begins its rescue mode operation by switching maintenance indicator 20 to a maintenance required state (e.g., a yellow visual display in one embodiment), by flashing the "rescue" light associated with resume/rescue switch 18 and the indicator lights on diagnostic display panel 36, and by performing a lid opened self-test.

During the lid opened self-test, processor 74 checks at least the following: 1) the charge state of battery 80; 2) the interconnection and operability of electrodes 50; 3) the state of event memory 78; 4) the functionality of real time clock 79; and 5) the functionality of A/D converter 91. The charge state of battery 80 is checked by monitoring the voltage level signals provided by power generation circuit 84. If battery 80 is determined to have a low charge, the "battery status" indicator 38 on diagnostic display panel 36 will be illuminated by processor 74 to indicate the sensed status. The interconnection and operability of electrodes 50 are checked by monitoring the impedance signals provided by impedance measuring circuit 90. If electrodes 50 are missing or unplugged from connector 32, or if electrodes 50 are damaged, processor 74 will illuminate "Electrodes" indicator light 40 on diagnostic display panel 36. Further, the functionality of real time clock 79 and A/D converter 91 is checked by monitoring the outputs of these circuit elements for expected signals. Diagnostic display panel "service" light 42 is illuminated by processor 74 if faults are identified in either of real time clock 79 or A/D converter 91.

If the lid opened self-test is successfully completed, processor 74 switches maintenance indicator 20 to an operational state. If a firmware card 29 is not present in card slot 24 and a serial cable is not plugged into the AED 10 at serial connector port 23, the processor 74 initiates the rescue mode of operation of AED 10. The rescue mode of operation generates audible voice prompts through speaker 34 to guide the user through the operations of AED 10 and if necessary, delivery of a defibrillation pulse to a stricken patient. AED 10 determines its rescue mode steps of operation by monitoring the impedance across electrode connector 32 and by monitoring the patient's cardiac rhythm sensed at electrodes 50.

The closing of lid 27 after rescue mode operation activates lid switch 25, which in turn activates processor 74 to initiate and perform a lid closed self-test. During the lid closed self-test, processor 74 performs a comprehensive check of the status and functionality of AED 10, including: 1) the state of event memory 78; 2) the functionality of real time clock 79; 3) the functionality of A/D converter 91; 4) the functionality of program memory 76, data memory 77 and event memory 78; 5) the charge state of battery 80; and 6) the interconnection and operability of electrodes 50. The state of event memory 78, the state of battery 80, the interconnection and operability of electrodes 50, and the functionality of real time clock 79 and A/D converter 91 are checked in a manner identical to that described above with reference to the lid opened self-test.

Conventional memory test routines are implemented to check the functionality of program memory 76, data memory 77 and event memory 78. Maintenance indicator 20 is switched to its maintenance required state by processor 74 if faults are identified during the lid closed self-test in order to alert the operator that maintenance is required. No audible alarms are actuated if faults are identified in the charge state of battery 80 or the interconnection or functionality of electrodes 50 during the lid closed self-test.

A daily self-test is initiated and performed by processor 74 at a predetermined time each day (i.e., every twenty-four hours). During the daily self-test, processor 74 performs all the component check operations described above that are performed during the lid opened and lid closed self-tests. In addition to illuminating the appropriate lights on diagnostic display panel 36, processor 74 switches maintenance indicator 20 to its maintenance required state if faults are identified during the daily self-test.

Processor 74 also initiates and performs a weekly self-test at a predetermined time one day each week. During the weekly self-test processor 74 performs all the component check operations described above that are performed during the daily self-test. In addition, processor 74 causes high voltage generation circuit 83 to sequentially operate in its charge and discharge modes, with the charge being dumped to internal resistive load 85. While high voltage generation circuit 83 is operating in the charge mode, processor 74 monitors the time required to charge the circuit's capacitors and the capacitor voltage. A fault is identified if either is out of nominal conditions. Maintenance indicator 20 and alarm 88 are actuated in the manner described above if any faults are identified during the weekly self-test. Note that all performed test and patient data may be recorded in event memory 78.

Watch dog timer 86 is set to time watch dog time-out periods of about thirty hours (i.e., a period greater than twenty-four hour periods between daily self-tests), and is reset by processor 74 at the beginning of each daily self-test and each time lid 27 is opened activating lid switch 25. In the event control system 72 malfunctions and watch dog timer 86 times out, internal hardware then switches maintenance indicator 20 to the maintenance required state and actuates alarm 88 to alert an operator to the fact that AED 10 requires maintenance.

AED 10 facilitates archival storage of rescue information in that data representative of the operation of AED 10, patient data, including the monitored cardiac rhythm of the patient, AED analysis of the patient data, key events detected during the rescue operation, and sound occurring within the immediate vicinity of AED 10 are stored in event memory 78 during rescue mode operation. However, if data card 29, which is preferably a memory card commonly known as a flashcard, is inserted into card slot 24 before beginning the rescue attempt, the rescue information is automatically recorded by data recorder 95 onto data card 29 thereby also facilitating archival storage of rescue information. The data card 29 is preferably a memory card having a RAM storage capability of 4, 8, 10, or 15 megs capacity.

Data card 29 is capable of storing up to twenty minutes of rescue information and sound. With data card 29 inserted, the default settings of AED 10 are such that sound is automatically recorded. The sound recording capability may be disabled, however thereby extending the time that rescue information may be recorded on data card 29 up to five hours.

Note that if data card 29 is inserted already containing previously stored rescue data, a voice prompt will be issued that says "Card full. Storing internally". If upon hearing this prompt, the operator ejects the full data card 29 and inserts an empty data card 29 before placing electrodes 50 on the patient, rescue data will then be stored on the new data card 29. If full card 29 is left in slot 24 when electrodes 50 are placed on the patient, rescue information will then be stored in AED event memory 78.

Stored data representative of the operation of AED 10 includes the real time of the occurrence of each of the following events: 1) the placement of electrodes 50 on the patient, 2) the initiation of the cardiac rhythm analysis voice prompt, 3) the initiation of the charging voice prompt, 4) the completion of the charge mode operation of high voltage generation circuit 83, and 5) the actuation of the rescue/resume switch 18 in the rescue mode. The actual time base of the patient's cardiac rhythm, e.g., EKG information, is also stored.

Following a rescue, the stored data can be retrieved from event memory 78 through the use of a personal computer (PC) 93 interfaced to serial connector port 23. Real time clock 79 can also be set through the use of PC 93 interfaced to communications port 22. If the stored data were stored on data card 29 and data card 29 remains in slot 24, the data may also be retrieved through the use of PC 93 interfaced to serial connector port 23. Alternatively, the data card 29 may be ejected from AED 10 and inserted into an appropriate card reader 94 that is directly connected to PC 93, such as a PCMCIA type I card reader.

PC 93 may be used to clear event memory 78 and/or data card 29 of previous rescue information when PC 93 is connected to AED 10 through serial connector port 23. The data card reader 94 of PC 93 may also be used to clear the memory of data card 29. Once rescue information is retrieved from event memory 78 or from data card 29 by PC 93, PC 93 may then be used to enter additional information to help identify the rescue information. This additional information may include patient name, medical identification, name of the responder who performed the rescue and the serial number of AED 10. PC 93 can be used to display all data to the user and to keep logs of performance.

Upon the completion of each lid opened, lid closed, daily and weekly self-test, processor 74 causes a record of the self-test to be stored in event memory 78. Each stored record includes data representative of the date and time of the test and the results of the test. The test results are recorded in the form of a code or other description indicating whether all the functions, components and component status states passed the test, or indicating the nature of any identified faults. In one embodiment, only the records of the twenty most recently performed tests are stored in memory 78. The stored self-test records can be retrieved from memory 78 through PC 93 interfaced to serial connector port 23.

In operation to perform a rescue intervention, when the lid 27 of the AED 10 is opened activating lid switch 25, voice prompts guide an operator through the rescue procedure. Once the electrodes 50 have been placed on the victim, the AED 10 analyzes the victim's cardiac rhythm. If the AED 10 detects a shockable cardiac rhythm, the voice prompt will say "Charging" and the AED 10 will charge preparatory to delivering a pulse or series of pulses to the victim. If the AED 10 does not detect a shockable rhythm at electrodes 50, the voice prompt will say "Check pulse. If no pulse, give CPR". Patient indications sensed at electrodes 50 in conjunction with further prompts from the AED 10 enable the operator to effectively deliver the CPR to the victim.

Figure 6:
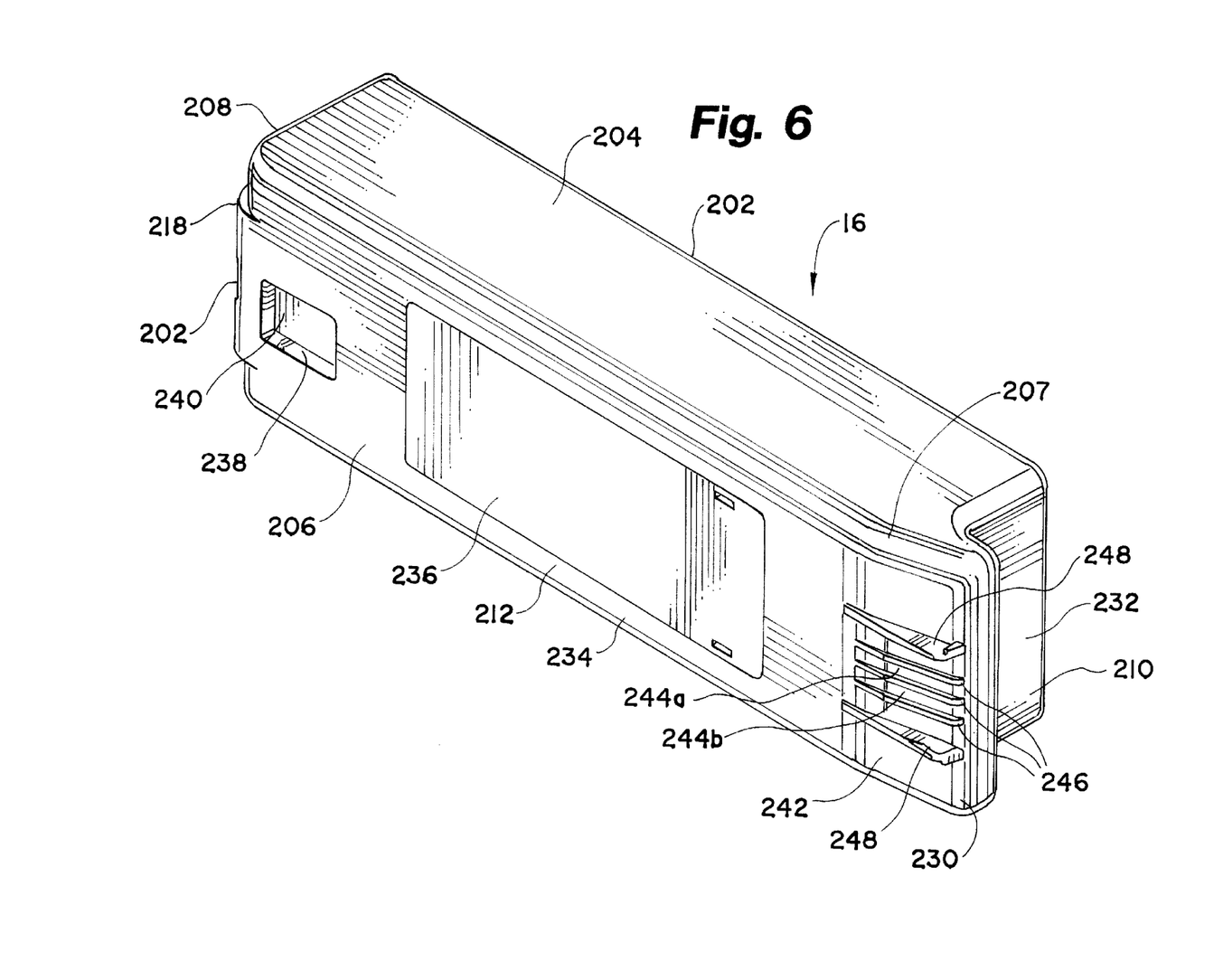
FIG. 6 is a front perspective view of the battery pack of the present invention.
Figure 7:
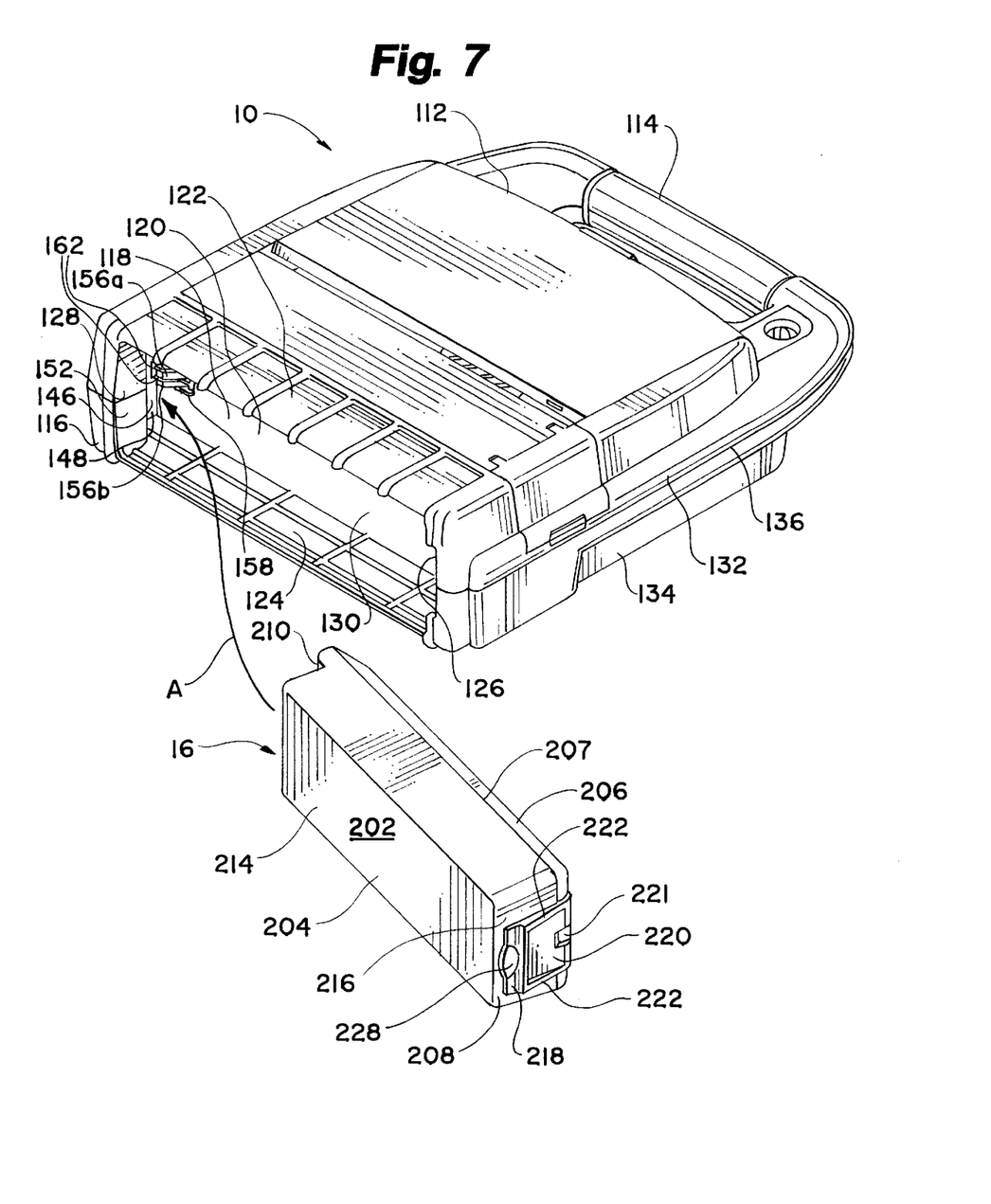
FIG. 7 is a rear perspective view of the battery pack disengaged from the AED.

Referring to FIGS. 6–12, generally, the AED of the present invention is depicted at 10 (FIG. 7). The AED 10 has a front side 112 with a carrying handle 114 formed thereon. The opposed rear side 116 includes the battery pack compartment 118. The battery pack compartment 118 is an enclosure 120 defined by top wall 122, opposed bottom wall 124, latch sidewall 126, hinge sidewall 128, and floor 130.

Figure 12:
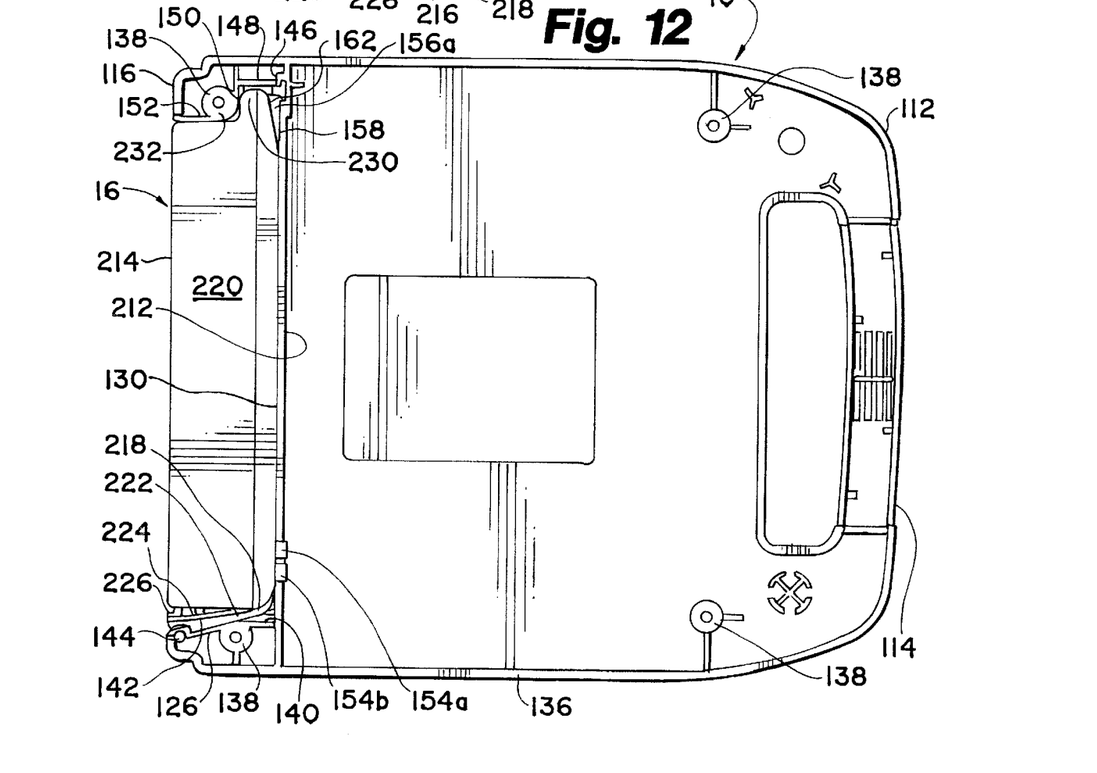
FIG. 12 is a top planar view of the bottom half of the AED with the battery pack engaged therewith.

The AED 10 is formed of a top half 132 and a bottom half 134 joined along a mating juncture 136. As depicted in FIG. 12, connecting posts 138 comprise screw receivers for joining the top half 132 and the bottom half 134 in cooperation with a screw (not shown) threaded into a bore defined in the upper margin of the connecting posts 138.

The latch sidewall 126 has a perpendicular wall portion 140 (FIG. 12) that is disposed generally perpendicular to floor 130 and is coupled thereto. An angled wall portion 142 extends outwardly from the perpendicular wall portion 140. A latch catch 144 is formed proximate the distal end of the angled wall portion 142.

The hinged sidewall 128 (FIGS. 7 and 12) includes a recessed receiver 146 defined in part by top wall 122 and bottom wall 124 in conjunction with the perpendicular wall portion 148 (perpendicular to floor 130) and parallel wall portion 150 (parallel to floor 130) of the hinge sidewall 128. The hinge sidewall 128 includes a second perpendicular wall portion 152 (perpendicular to floor 130) extending outward from the parallel wall portion 150.

Figure 8:
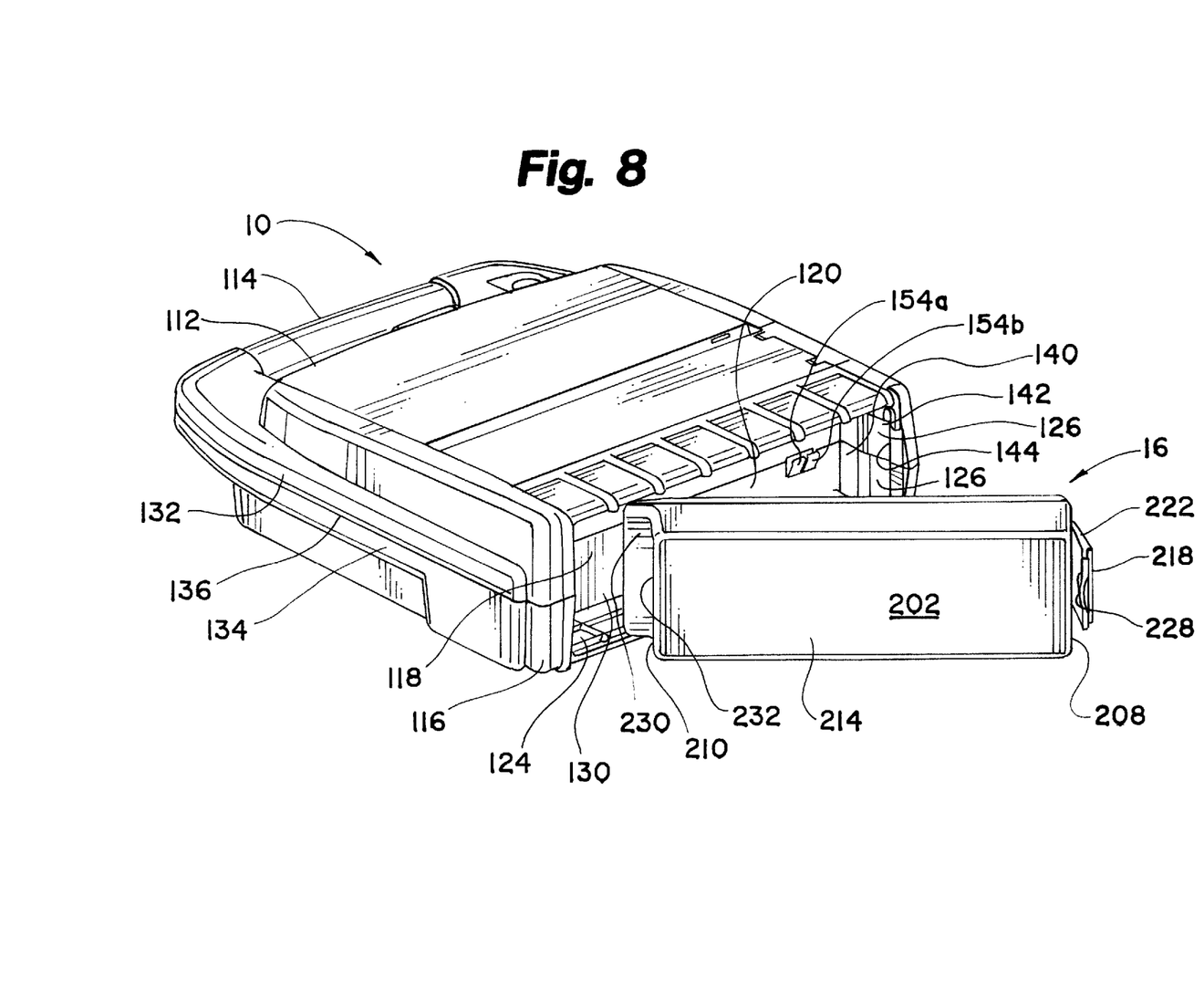
FIG. 8 is a rear perspective view of the battery pack positioned with respect to the AED just prior to engagement therewith.
Figure 9:
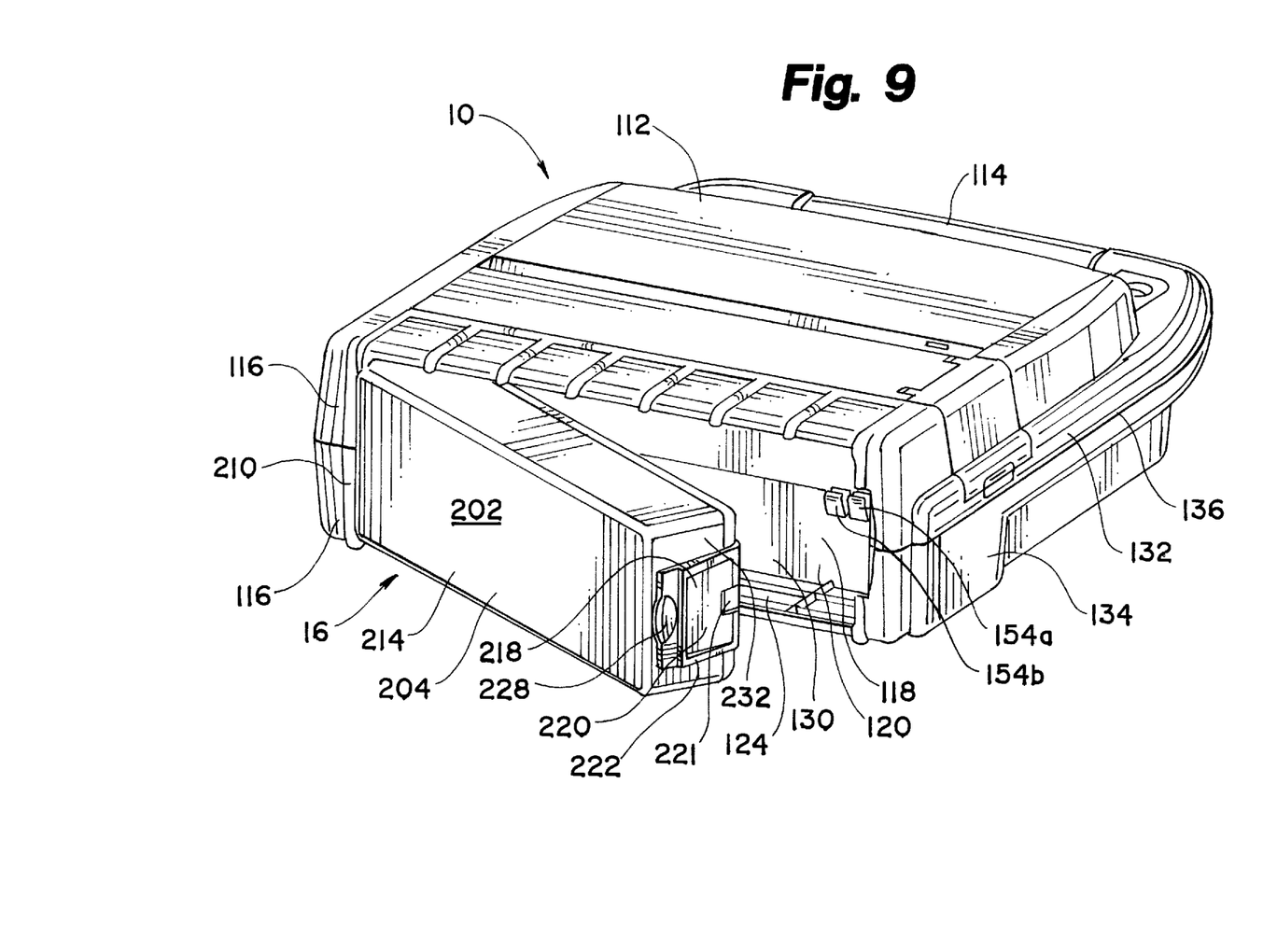
FIG. 9 is a rear perspective view of the battery pack with the hinge end thereof partially engaged with the AED.

The first and second battery-installed detector electrodes 154a, 154b (FIGS. 8, 9, and 12) are disposed in the floor 130 of the battery pack compartment 118. As depicted in FIGS. 8 and 9, electrodes 154a, 154b have a lower end that is fixedly coupled to the floor 130 with the upper, distal end thereof being free of engagement therewith. The electrodes 154a, 154b are preferably made of a resilient, deflectable metallic material. The electrodes 154a, 154b are deflectable with respect to the fixed lower end thereof. Further, the electrodes 154a, 154b are biased outward from the lower fixed end, such that the electrodes 154a, 154b resist a force tending to move them toward the floor 130. The electrodes 154a, 154b are preferably disposed proximate the latch sidewall 126 of the battery pack compartment 118. The electrodes 154a, 154b are in electrical communication with the electronic components of the AED 10, including the processor 74, described above in conjunction with AED 10. The electrodes 154a, 154b are spaced apart such that the electrodes 154a, 154b are not in electrical communication with each other.

Referring to FIGS. 7 and 12, the main battery electrodes 156a, 156b are also disposed in floor 130 of the battery pack compartment 118. The main battery electrodes 156a, 156b are proximate the hinge sidewall 128 of the battery pack compartment 118. The electrodes 156a, 156b have a fixed (proximate) end 158 fixedly disposed within a recess 160 defined in the floor 130. The distal end 162 of each of the main battery electrodes 156a, 156b is free of engagement. Further, the distal end 162 of each of the main battery electrodes 156a, 156b is preferably radiused, forming a curved electrical contact surface. The curved electrical contact surface of the distal end 162 of the main battery electrodes 156a, 156b is biased outward away from the floor 130. The main battery electrodes 156a, 156b are preferably formed of a resilient, deflectable metallic material. The electrodes 156a, 156b are deflectable with respect to the fixed end 158 thereof. The main battery electrodes 156a, 156b are in electrical communication with the electronic components of the AED 10, including the processor 74.

The battery pack of the present invention is shown generally at 16 in FIGS. 6–12, 14, and 15. The battery pack 16 has a case 202 that is formed of case halves 204, 206 fixedly joined at a mating juncture 207. Generally, the battery pack 16 has a latch end 208, a hinge end 210, a forward face 212 and a rear face 214. When the battery pack 16 is engaged with the AED 10, the forward face 212 faces inward with respect to the battery pack compartment 118 and is disposed proximate and substantially parallel to the floor 130 of the battery pack compartment 118 when in the engaged disposition with the AED 10, the engaged disposition being depicted in FIG. 12.

Referring to FIGS. 7, 9–11, and 14–15, the latch end 208 of the battery pack 16 has a generally planar end wall 216 that is formed as a part of the case half 206. A latch 218 is formed integral with the case half 206 and extends alongside but is spaced apart from the end wall 216.

The latch 218 has a generally planar latch plate 220. The latch plate 220 has a groove 221 defined therein proximate the point of connection to the case half 206. A pair of outwardly extending ribs 222 are formed at the opposed sides of the latch plate 220. A catch face 224 is formed generally transverse to the plane of the latch plate 220 and extending between the ribs 222. An actuator tab 226 forms the distal end of the latch 218. The actuator tab 226 has a finger groove 228 formed therein to facilitate compressing the latch 218 against a bias designed into the latch 218. Such compression facilitates disengaging the catch face 224 of the latch 218 from the latch catch 144 for removal of the battery pack 16 from the AED 10.

Referring now to FIGS. 6, 8, 12, and 14–15, the hinge end 210 of the battery pack 16 has a receiver insert 230 formed thereon. The receiver insert 230 has a generally rounded outer surface and is designed to be received within the receiver 146 of the AED 10. An end wall 232 extends outward from the receiver insert 230 and is preferably generally parallel to the end wall 216 of the latch end 208.

Figure 10:
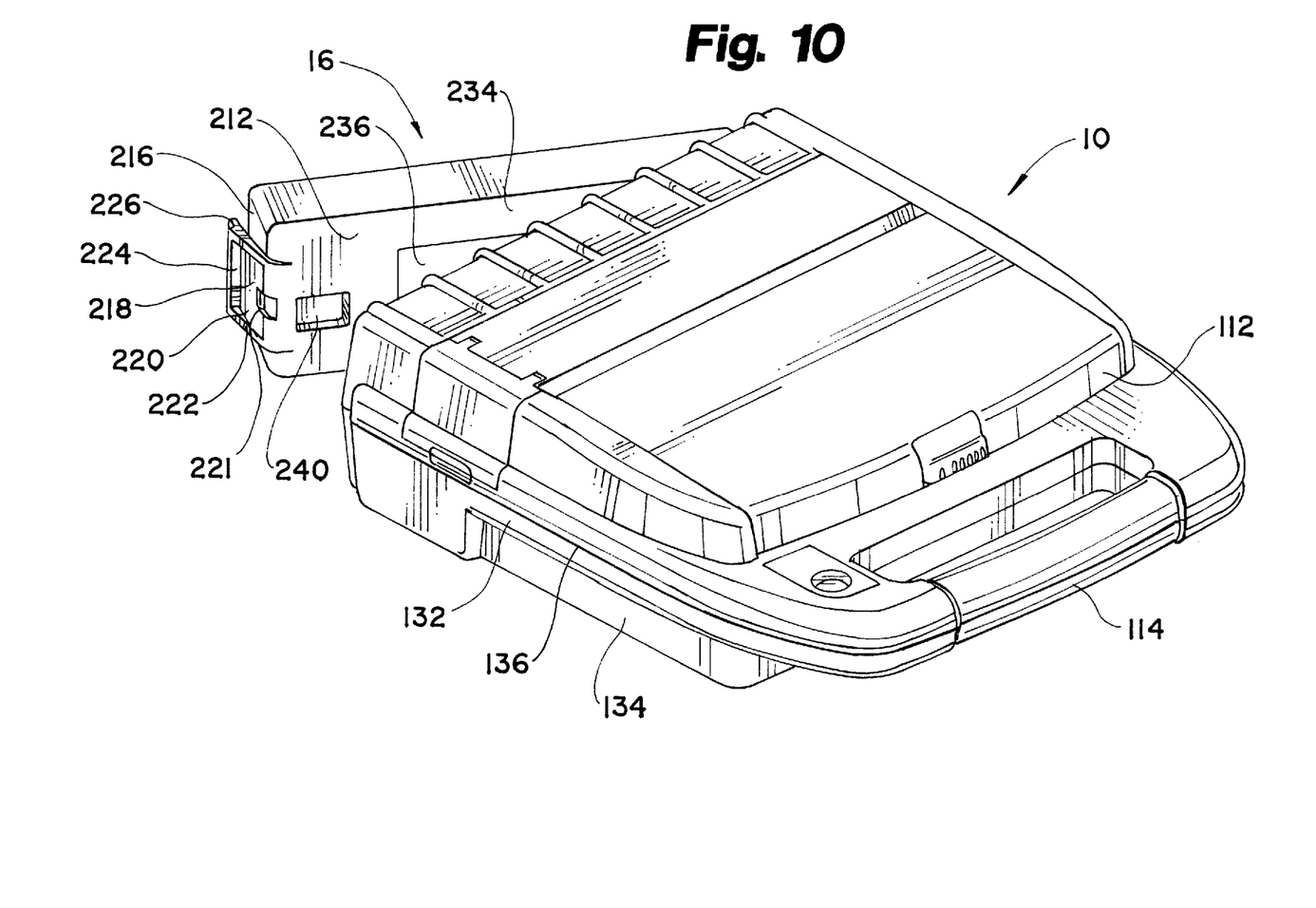
FIG. 10 is a front perspective view of the battery pack and AED positioned as depicted in FIG. 9.

Turning to FIGS. 6 and 10, the forward face 212 of the case 202 of the battery pack 16 has a generally planar portion 234 extending from the latch end 208 to a position proximate the receiver insert 230. The planar portion 234 has an access panel 236 that may be removed to gain access to the plurality of battery cells disposed within the battery pack 16. A plate recess 238 is formed in the planar portion 234 proximate the latch end 208. A preferably metallic conductor plate 240 is disposed within the plate recess 238. When the battery pack 16 is in the engaged disposition with the AED 10, the conductor plate 240 is in registry with the battery-installed detector electrodes 154a, 154b. In such disposition, the conductor plate 240 is formed of an electrically conductive material and is in electrical communication with both the battery-installed detector electrodes 154a, 154b. The conductor plate 240 completes an electrical circuit between the battery-installed detector electrodes 154a and 154b.

An inclined portion 242 of the forward face 212 extends from the planar portion 234 to the receiver insert 230. The inclined portion 242 has at least two electrodes 244a, 244b disposed thereon. The electrodes 244a, 244b are in electrical communication with the battery cells disposed within the battery pack 16. The electrodes 244a, 244b are preferably generally elongate, flat metallic strips and are disposed between electrode rib separators 246, formed in the inclined portion 242. When the battery pack 16 is in the engaged disposition with the AED 10, the electrodes 244a, 244b are in registry with the main battery electrodes 156a, 156b. The electrode 244a is in electrical communication with the main battery electrode 156a and the electrode 244b is in electrical communication with the main battery electrode 156b when in such disposition. A pair of end guides 248 are disposed on one side of the electrodes 244a, 244b.

Figure 11:
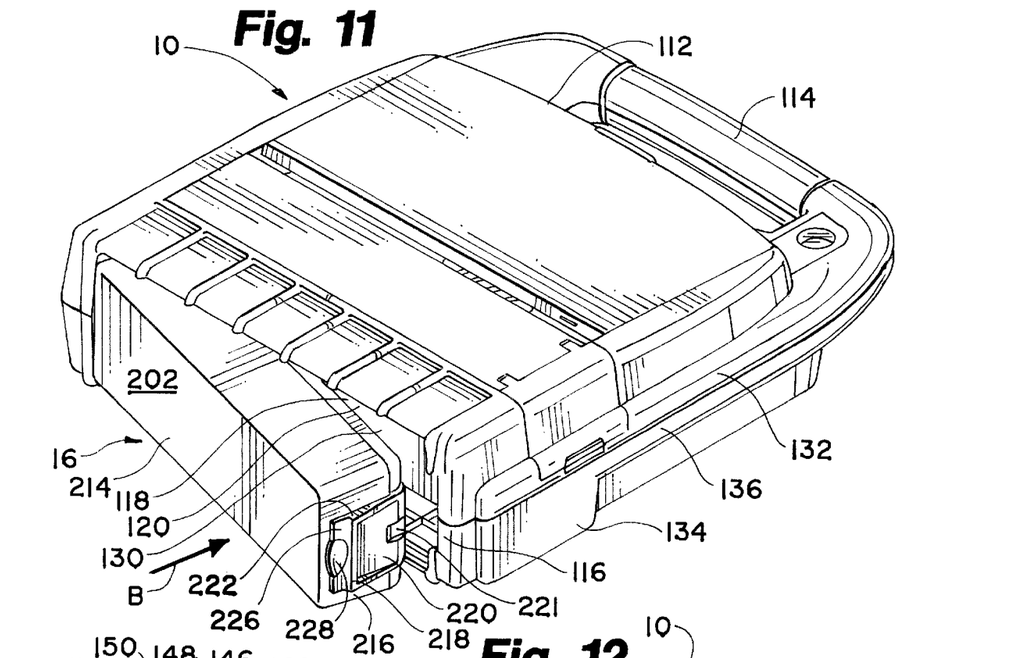
FIG. 11 is a rear quarter perspective view of the battery pack being rotated into engagement with the AED in a position just prior to engagement of the latch end of the battery pack with the AED.

To bring the battery pack 16 into operative engagement with the AED 10, the battery pack 16 is moved with respect to the AED 10 as indicated by Arrow A in FIG. 17. Such movement brings the battery pack 16 first into a position as depicted in FIG. 9 and then into a disposition as depicted in FIG. 11. In the disposition as depicted in FIG. 9, the receiver insert 230 is partially received within the receiver 146. In this disposition, the battery-installed detector electrodes 154a, 154b are not in contact with the conductor plate 240 and the main battery electrodes 156a, 156b are not in electrical contact with the electrodes 244a, 244b.

Turning now to FIG. 11, the battery pack is rotated into the battery pack compartment 118 defined in the rear side 116 of the AED 10 as indicated by the Arrow B. At approximately the disposition as indicated in FIG. 11, the main battery electrodes 156a, 156b make electrical contact with the electrodes 244a, 244b and electrical power could be provided by the battery pack 16 to the processor 74 in the AED 10. The battery-installed detector electrodes 254a, 254b, however, are still not in electrical contact with the conductor plate 240.

FIG. 12 depicts the battery pack 16 in operable engagement with the AED 10. In the transition between the disposition depicted in FIG. 11 and that depicted in FIG. 12, the latch 218 is compressed toward the end wall 216 by the action of the ribs 222 riding on the latch sidewall 126 of the battery pack compartment 118. When the catch face 224 of the latch 218 clears the latch catch 144 of the latch sidewall 126, the resilient latch 218 snaps outward with the catch face 224 thereof engaging at the latch catch 144.

In the operable engaged disposition as indicated in FIG. 12, the conductor plate 240 is in both compressive and electrical contact with the battery-installed detector electrodes 154a, 154b. This contact has two functions. First, the conductor plate 240 functions as a switch making an electrical contact between the battery-installed detector electrodes 154a, 154b. Second, by being in compressive engagement therewith, the battery-installed detector electrodes 154a, 154b, exert an outwardly directed bias on the battery pack 16, thereby preventing the battery pack 16 from rattling within the battery pack compartment 118.

In the operably engaged disposition as depicted in FIG. 12, the main battery electrodes 156a, 156b are in electrical communication with the electrodes 244a, 244b of the battery pack 16. Accordingly, the battery pack 16 is disposed such that energy is available to the AED 10.

Figure 13:
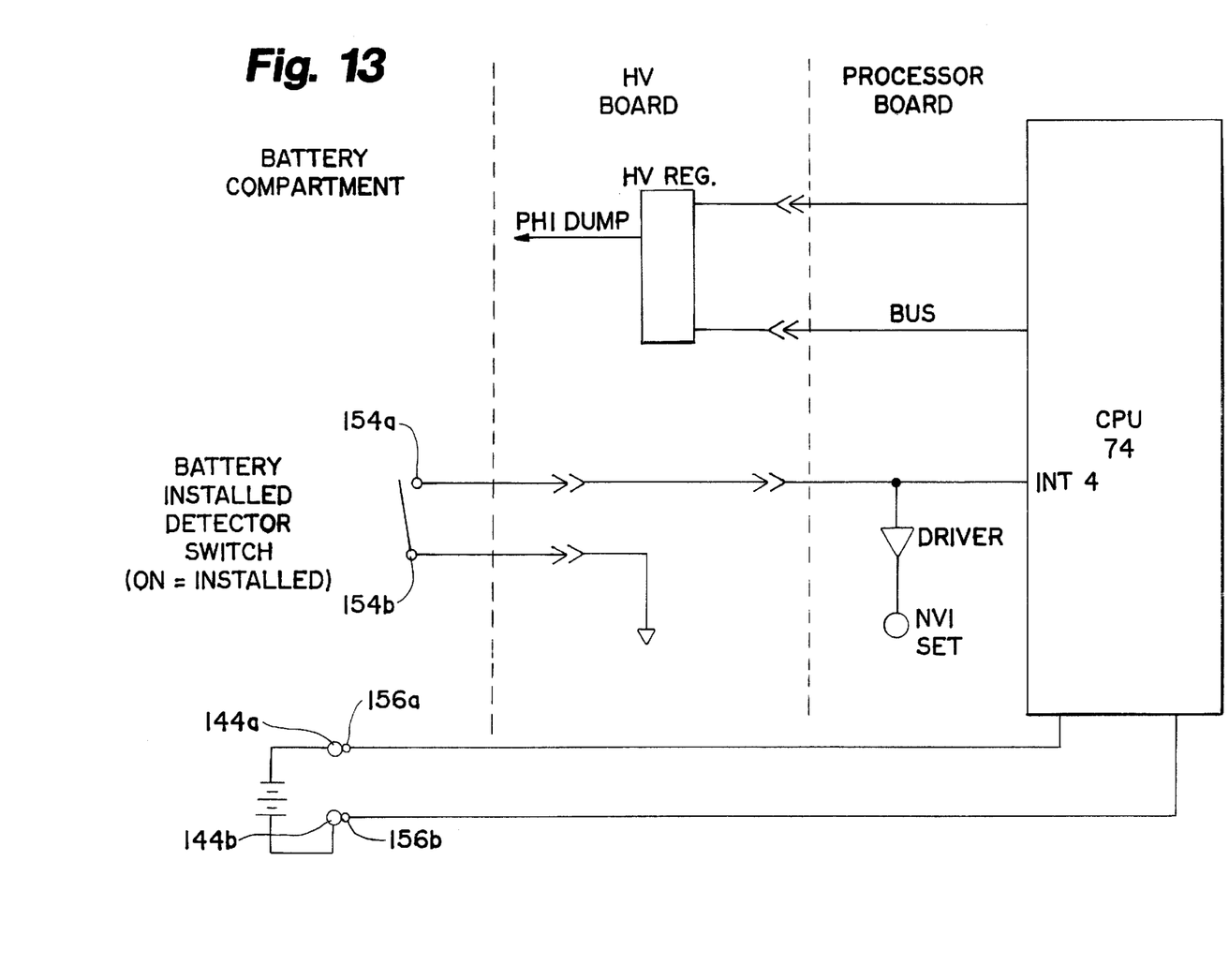
FIG. 13 is a schematic diagram of the battery removal safety circuit of the present invention.
Figure 14:
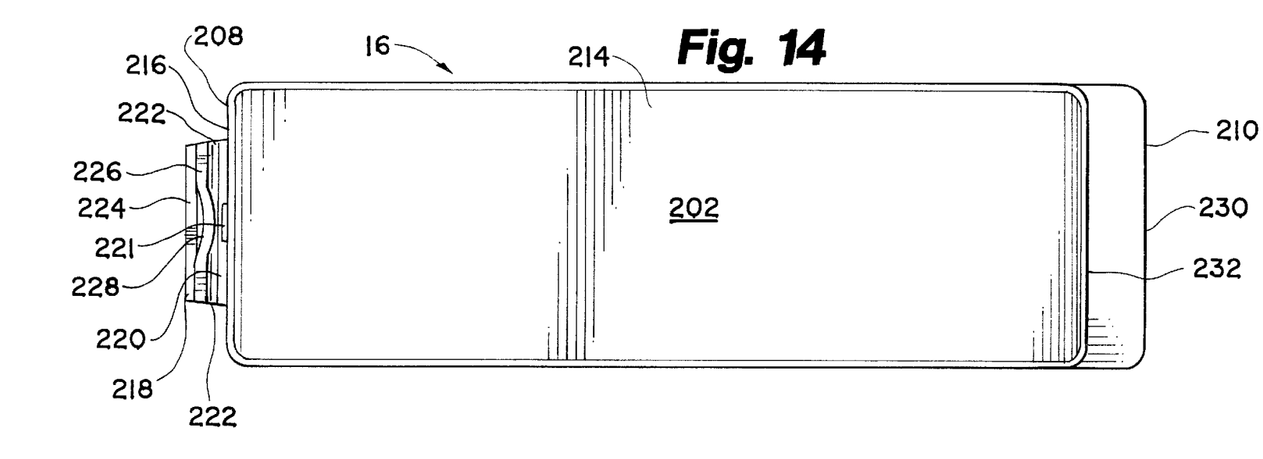
FIG. 14 is a rear elevational view of the battery pack.
Figure 15:
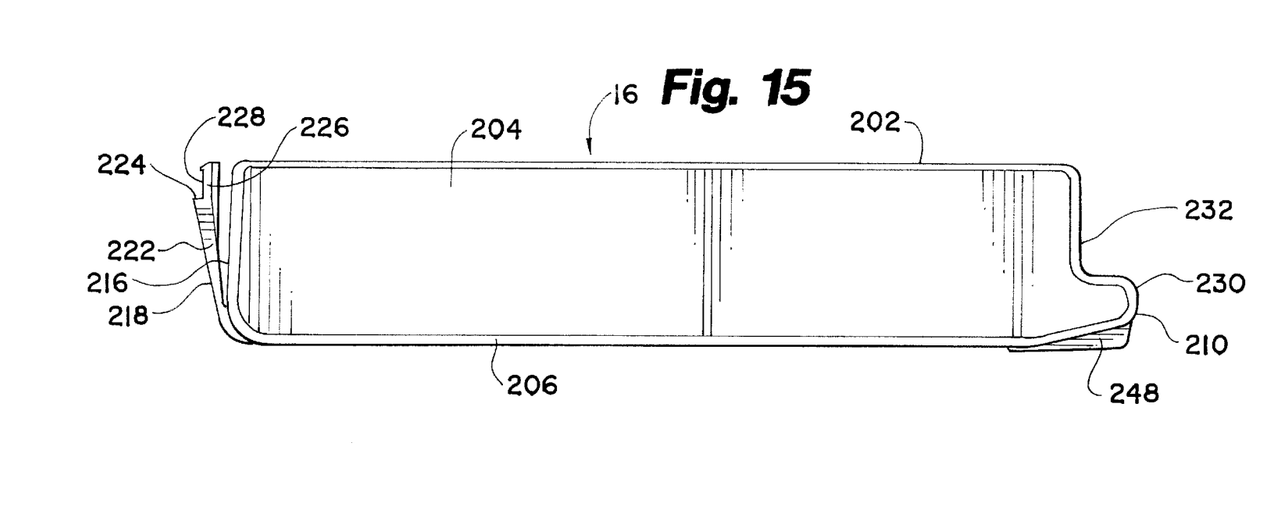
FIG. 15 is a top elevational view of the battery pack.

To remove the battery pack 16 from the AED 10, the finger groove 228 is engaged and depressed to bring the latch 218 closer to the end wall 216. When the catch face 224 is free of engagement with the latch catch 144, the battery pack 16 may be rotated out of the battery pack compartment 118 by a rotational motion opposite to that as indicated by Arrow B in FIG. 11. Such rotational motion progressively electrically disengages the battery pack 16 from the AED 10. The first bit of such rotation, breaks the engagement between the conductor plate 240 and the battery-installed detector electrodes 154a, 154b. This breaks the circuit that existed between the battery-installed detector electrodes 154a and the battery-installed detector electrodes 154b. Such opening of the previously existing circuit provides an anticipatory indication to the processor 74 that disengagement of the battery pack from the AED is imminent. This condition is schematically depicted in FIG. 13.

At this point, the main battery electrodes 156a, 156b are still in electrical communication with the electrodes 244a, 244b of the battery pack 16. Accordingly, energy is still being supplied from the battery pack 16 to the processor 74 of the AED 10. In the usual rotation of the battery pack 16 out of the battery pack compartment 118, there is at least a 40 millisecond period of time between when the electrical circuit between the battery-installed detector electrodes 154a, 154b is broken and when the main battery electrodes 156a, 156b are disengaged from the electrodes 244a, 244b. In this period of time, the processor 74 is still powered and detects that the battery is no longer installed. The processor 74 then commands the high voltage board to dump all charges existing in the high voltage capacitors. This dump is accomplished on an orderly basis in such 40 millisecond period before the disengagement of the main battery electrodes 156a, 156b and electrodes 244a, 244b under power of the battery pack 16. At the time of such disengagement, the processor 74 of the AED 10 goes dead for lack of power from the battery pack 16.

Although the present invention has been described with reference to preferred embodiments, those skilled in the art will recognized that changes can be made in form and detail without departing from the spirit and scope of the invention.

What is claimed is:

1. A battery pack for being removably disposed in operable engagement with an AED, the AED having electronic circuitry disposed within an AED housing for delivery of an electric shock to a stricken patient, comprising:
   a battery pack housing;
   at least one battery disposed in the battery pack housing;
   at least two battery electrodes being in electric communication with the at least one battery for being disposed in operational engagement with the AED for transmission of power thereto; and
   anticipatory detector means operably coupled to the battery pack housing and being communicatively coupled to the AED electronic circuitry when the battery pack is in operational engagement with the AED for generating an anticipatory signal communicated to the AED electronic circuitry, said signal indicating that disengagement of the battery pack from the AED is imminent.

2. The battery pack as claimed in claim 1 wherein the anticipatory detector means comprises a conductive plate disposed on an external surface of the battery pack housing.

3. The battery pack as claimed in claim 1 wherein the anticipatory detector means establishes a circuit between a first and a second electrode when the battery pack is disposed in operable engagement with the AED, the first and the second electrodes being communicatively coupled to the AED electronic circuitry.

4. The battery pack as claimed in claim 3 further including the at least two battery electrodes being disposed on an external surface of the battery pack housing, the at least two battery electrodes being spaced apart from the anticipatory detector means and the at least two battery electrodes establishing a circuit with complimentary electrodes disposed on the AED when the battery pack is disposed in operable engagement with the AED for providing power to said complimentary electrodes, the complimentary electrodes being communicatively coupled to the AED electronic circuitry whereby said power powers the AED electronic circuitry.

5. The battery pack as claimed in claim 4 wherein disengagement of the battery pack from the disposition in operable engagement with the AED acts to break the circuit established between the anticipatory detector means and the first and the second electrodes prior to breaking the circuit established between the at least two battery electrodes and the complimentary electrodes disposed on the AED.

6. The battery pack as claimed in claim 4 wherein, during disengagement of the battery pack from the disposition in operable engagement with the AED, the battery pack continues to power the AED electronic circuits by means of the circuit established between the at least two battery electrodes and the complimentary electrodes disposed on the AED for a finite period of time subsequent to breaking the circuit established between the anticipatory detector means and the first and the second electrodes.

7. The battery pack as claimed in claim 1 further including the battery pack housing having a latch end and an opposed hinge end, the latch end having a latch disposed thereon for latching engagement with cooperative latch structure of the AED, and the hinge end having a disengageable hinge portion defining a hinge in cooperation with hinge structure of the AED.

8. The battery pack as claimed in claim 7 wherein disengagement of the battery pack from operable engagement with the AED is effected by rotational motion of the battery pack about the hinge structure of the AED, said rotational motion acting to progressively disengage first the anticipatory detector means and second the at least two battery electrodes from operational engagement with the AED.

9. An AED, comprising:
   a housing
   electronic circuitry disposed in the housing for delivery of an electric shock to a stricken patient;
   a removable battery pack being selectively operably, communicatively coupled to the electronic circuitry, the battery pack having an anticipatory detector means for generating an anticipatory signal to the electronic circuitry, said signal indicating that the disengagement of the battery pack from the AED is imminent.

10. The AED as claimed in claim 9 wherein the anticipatory detector means comprises a conductive plate disposed on an external surface of the battery pack housing.

11. The AED as claimed in claim 9 wherein the anticipatory detector means establishes a circuit between a first and a second electrode when the battery pack is disposed in operable engagement with the AED, the first and the second electrodes being communicatively coupled to the AED electronic circuitry.

12. The AED as claimed in claim 11 further including the at least two battery electrodes being disposed on an external surface of the battery pack housing, the at least two battery electrodes being spaced apart from the anticipatory detector means and the at least two battery electrodes establishing a circuit with complimentary electrodes disposed on the AED when the battery pack is disposed in operable engagement with the AED for providing power to said complimentary electrodes, the complimentary electrodes being communicatively coupled to the AED electronic circuitry whereby said power powers the AED electronic circuitry.

13. The AED as claimed in claim 12 wherein disengagement of the battery pack from the disposition in operable engagement with the AED acts to break the circuit established between the anticipatory detector means and the first and the second electrodes prior to breaking the circuit established between the at least two battery electrodes and the complimentary electrodes disposed on the AED.

14. The AED as claimed in claim 12 wherein, during disengagement of the battery pack from the disposition in operable engagement with the AED, the battery pack continues to power the AED electronic circuits by means of the circuit established between the at least two battery electrodes and the complimentary electrodes disposed on the AED for a finite period of time subsequent to breaking the circuit established between the anticipatory detector means and the first and the second electrodes.

15. The AED as claimed in claim 9 further including the battery pack housing having a latch end and an opposed hinge end, the latch end having a latch disposed thereon for latching engagement with cooperative latch structure of the AED, and the hinge end having a disengageable hinge portion defining a hinge in cooperation with hinge structure of the AED.

16. The AED as claimed in claim 15 wherein disengagement of the battery pack from operable engagement with the AED is effected by rotational motion of the battery pack about the hinge structure of the AED, said rotational motion acting to progressively disengage first, the anticipatory detector means, and second, the at least two battery electrodes from operational engagement with the AED.

17. The AED as claimed in claim 10 wherein the first and a second electrodes are biased to exert a force on the anticipatory detector means, said force acting to hold the battery pack in substantially motionless operational engagement with the AED housing.

18. The AED as claimed in claim 14 wherein the complimentary electrodes disposed on the AED are biased into compressive engagement with the at least two battery electrodes of the battery pack, said bias acting to maintain the circuit established between the at least two battery electrodes and the complimentary electrodes during an initial rotational portion of the disengagement of the battery pack from the disposition in operable engagement with the AED.

19. The AED as claimed in claim 18 wherein the complimentary electrodes each have a proximal end being operably coupled to the AED and a distal end having a curved engaging portion for engaging one of the at least two battery electrodes, the curved engaging portion riding on the battery electrode and maintaining electrical communication therewith during the initial rotational portion of the disengagement of the battery pack from the disposition in operable engagement with the AED.

20. In an AED having electronic circuitry powered by a disengageable battery pack, including high voltage storage circuits controlled by a processor, a method for ensuring that the stored high voltage in the high voltage storage circuits of the AED is safely discharged during disengagement of the battery pack from the AED, comprising the steps of:

providing an anticipatory signal to the electronic circuitry, said signal indicating that the disengagement of the battery pack from the AED is imminent;

maintaining electrical communication between the battery pack and the processor for a finite period of time after commencement of the disengagement of the battery pack from the AED; and discharging the high voltage circuits under control of the processor upon receipt of the anticipatory signal during the finite period of time.

* * * * *